(12) United States Patent
Michinaka et al.

(10) Patent No.: US 9,155,725 B2
(45) Date of Patent: Oct. 13, 2015

(54) ADHESIVE SKIN PATCH AND PACKAGED PRODUCT

(75) Inventors: Yasunari Michinaka, Tsukuba (JP); Yuka Ansai, Tsukuba (JP)

(73) Assignee: Hisamitsu Pharmaceutical CO., INC., Tosu-shi, Saga (JP)

( * ) Notice: Subject to any disclaimer, the term of this patent is extended or adjusted under 35 U.S.C. 154(b) by 164 days.

(21) Appl. No.: 12/919,743

(22) PCT Filed: Feb. 9, 2009

(86) PCT No.: PCT/JP2009/052180
§ 371 (c)(1),
(2), (4) Date: Nov. 10, 2010

(87) PCT Pub. No.: WO2009/107478
PCT Pub. Date: Sep. 3, 2009

(65) Prior Publication Data
US 2011/0195109 A1    Aug. 11, 2011

(30) Foreign Application Priority Data
Feb. 27, 2008  (JP) ................ 2008-046805

(51) Int. Cl.
*A61F 13/02* (2006.01)
*A61K 31/40* (2006.01)
*A61L 15/16* (2006.01)
*A61K 31/4045* (2006.01)
*A61K 9/70* (2006.01)

(52) U.S. Cl.
CPC ........... *A61K 31/4045* (2013.01); *A61K 9/7053* (2013.01); *A61K 9/7076* (2013.01)

(58) Field of Classification Search
None
See application file for complete search history.

(56) References Cited

U.S. PATENT DOCUMENTS

| | | | |
|---|---|---|---|
| 5,059,189 A | 10/1991 | Cilento et al. | |
| 5,676,968 A | 10/1997 | Lipp et al. | |
| 5,807,570 A * | 9/1998 | Chen et al. | 424/449 |
| 5,830,497 A | 11/1998 | Yamanaka et al. | |
| 5,866,157 A | 2/1999 | Higo et al. | |
| 6,146,656 A | 11/2000 | Hori et al. | |
| 6,207,183 B1 | 3/2001 | Horstmann et al. | |
| 6,620,429 B1 | 9/2003 | Müller | |
| 6,638,528 B1 | 10/2003 | Kanios | |
| 6,884,434 B1 | 4/2005 | Muller et al. | |
| 6,899,894 B1 | 5/2005 | Klein et al. | |
| 7,150,881 B2 | 12/2006 | Govil et al. | |
| 7,175,853 B1 * | 2/2007 | Bracht | 424/449 |
| 7,921,999 B1 * | 4/2011 | Kimball | 206/440 |
| 2002/0192243 A1 | 12/2002 | Hsu et al. | |
| 2003/0104041 A1 | 6/2003 | Hsu | |
| 2003/0180347 A1 | 9/2003 | Young et al. | |
| 2004/0028724 A1 | 2/2004 | Terahara et al. | |
| 2004/0096491 A1 * | 5/2004 | Tateishi et al. | 424/449 |
| 2004/0220262 A1 | 11/2004 | Hsu et al. | |
| 2005/0074487 A1 | 4/2005 | Hsu et al. | |
| 2006/0292210 A1 | 12/2006 | Inosaka et al. | |
| 2007/0098772 A1 | 5/2007 | Westcott et al. | |
| 2009/0203797 A1 | 8/2009 | Kawahara et al. | |
| 2009/0220580 A1 * | 9/2009 | Kawahara et al. | 424/449 |
| 2010/0062046 A1 | 3/2010 | Allen et al. | |
| 2011/0086086 A1 | 4/2011 | Johnson et al. | |

FOREIGN PATENT DOCUMENTS

| | | | |
|---|---|---|---|
| EP | 387751 A2 | | 9/1990 |
| EP | 0 887 075 A2 | | 12/1998 |
| EP | 1366762 | | 12/2003 |
| EP | 1542177 | | 6/2005 |
| EP | 1 743 645 | * | 1/2007 |
| JP | H7506083 | | 7/1995 |
| JP | H1135452 | | 2/1999 |
| JP | H1147233 | | 2/1999 |
| JP | H1160475 A | | 3/1999 |
| JP | 11506462 A | | 6/1999 |
| JP | H11209270 A | | 8/1999 |
| JP | H11209271 A | | 8/1999 |
| JP | 2001-518058 A | | 10/2001 |
| JP | 2002-509874 A | | 4/2002 |
| JP | 2002-509878 A | | 4/2002 |
| JP | 2002509879 A | | 4/2002 |
| JP | 2003528045 A | | 9/2003 |
| JP | 2004083523 A | | 3/2004 |
| JP | 2005-528413 A | | 9/2005 |
| JP | 2005-535686 A | | 11/2005 |
| JP | 2007016019 A | | 1/2007 |
| JP | 2007016020 A | | 1/2007 |
| JP | 2007031436 | | 2/2007 |
| JP | 2007-176880 A | | 7/2007 |
| WO | 96/16642 A1 | | 6/1996 |
| WO | 96/39136 A1 | | 12/1996 |
| WO | 97/11696 | | 4/1997 |
| WO | 01/43734 A2 | | 6/2001 |

(Continued)

OTHER PUBLICATIONS

JP 2007-016020, machine translation, (published Jan. 25, 2007), pp. 1-15.*

(Continued)

Primary Examiner — Scott Long
Assistant Examiner — Lyndsey Beckhardt
(74) Attorney, Agent, or Firm — Nath, Goldberg & Meyer; Joshua B. Goldberg

(57) ABSTRACT

Provided is a patch 1 containing a backing layer 2 and a pressure-sensitive adhesive layer 3 formed on the backing layer 2, where the pressure-sensitive adhesive layer 3 contains (i) ropinirole and a metal salt produced by the reaction of a ropinirole acid adduct and a metal ion containing desalting agent in an equivalent mole or less to the acid adduct and (ii) an adhesive base free of a hydroxyl group and a carboxy group.

9 Claims, 1 Drawing Sheet

(56) References Cited

FOREIGN PATENT DOCUMENTS

| WO | 02/38139 | A1 | 5/2002 |
|---|---|---|---|
| WO | 02/45701 | A2 | 6/2002 |
| WO | 02/069942 | A1 | 9/2002 |
| WO | 2006/040680 | A1 | 4/2006 |
| WO | 2006/082728 | A1 | 8/2006 |
| WO | WO 2006-114868 | * | 11/2006 |
| WO | 2007/012963 | A1 | 2/2007 |
| WO | 2007/094385 | A1 | 8/2007 |
| WO | 2007/129712 | A1 | 11/2007 |
| WO | 2008/032678 | A1 | 3/2008 |

OTHER PUBLICATIONS

Form PCT/IB/338 (Notification of Transmittal of Translation of the International Preliminary Report on Patentability), mailed on Oct. 14, 2010, in International Application No. PCT/JP2009/052180, one (1) page.
English translation of the International Preliminary Report on Patentability (Chapter 1 of the Patent Cooperation Treaty), issued on Oct. 5, 2010, in International Application No. PCT/JP2009/052180, eight (8) pages.
International Preliminary Examination Report for a related PCT Application No. PCT/JP2009/052181; 8 pages; includes the PCT/IB/338, the PCT/IB/373, and the PCT/ISA/237; mailed on Oct. 14, 2010.
Extended European Search Report issued on Mar. 31, 2011, in counterpart European Patent Application No. 09715635.0.
International Preliminary Examination Report for a related PCT Application No. PCT/JP2009/052175; 6 pages; includes the PCT/IB/338, the PCT/IB/373, and the PCT/ISA/237; mailed on Oct. 14, 2010.
International Preliminary Examination Report for a related PCT Application No. PCT/JP2009/052177; 5 pages; includes the PCT/IB/338, the PCT/IB/373, and the PCT/ISA/237; mailed on Oct. 14, 2010.
Extended European Search Report issued Mar. 31, 2011, for European Application No. 09715476.9, seven (7) pages.
Extended European Search Report issued on Apr. 6, 2011, in related European Patent Application No. 09715573.3, five (5) pages.
Office Action issued for Japanese Patent Application No. P2010-500638 on Aug. 13, 2013.
Office Action issued for Japanese Patent Application No. P2010-500639 on Aug. 20, 2013.
USPTO Office Action, issued on Mar. 1, 2013, in U.S. Appl. No. 12/919,723, twenty one (21) pages.
Office Action issued by the U.S. Patent and Trademark Office on Sep. 21, 2012 for U.S. Appl. No. 12/919,723; 11 pages.
Office Action issued by the U.S. Patent and Trademark Office on Sep. 12, 2012 for U.S. Appl. No. 12/919,739; 9 pages.
Japanese Patent Application No. P2010-500640, Notification of Information Provision dated May 13, 2014, six (6) pages.
Search Report for EP 09715019.7; 8 pages; mailed on Jun. 12, 2013.
"Anonymous: Transdermal and topical drug delivery", Pharmaceutical Press, 2003, p. 110-p. 111, XP002697381.
Office Action issued in Japanese Patent Application No. P2010-500640 dated Sep. 24, 2013, 3 pages.
U.S. Appl. No. 12/919,739; Office Action dated Sep. 19, 2014, thirty-one (31) pages.

* cited by examiner

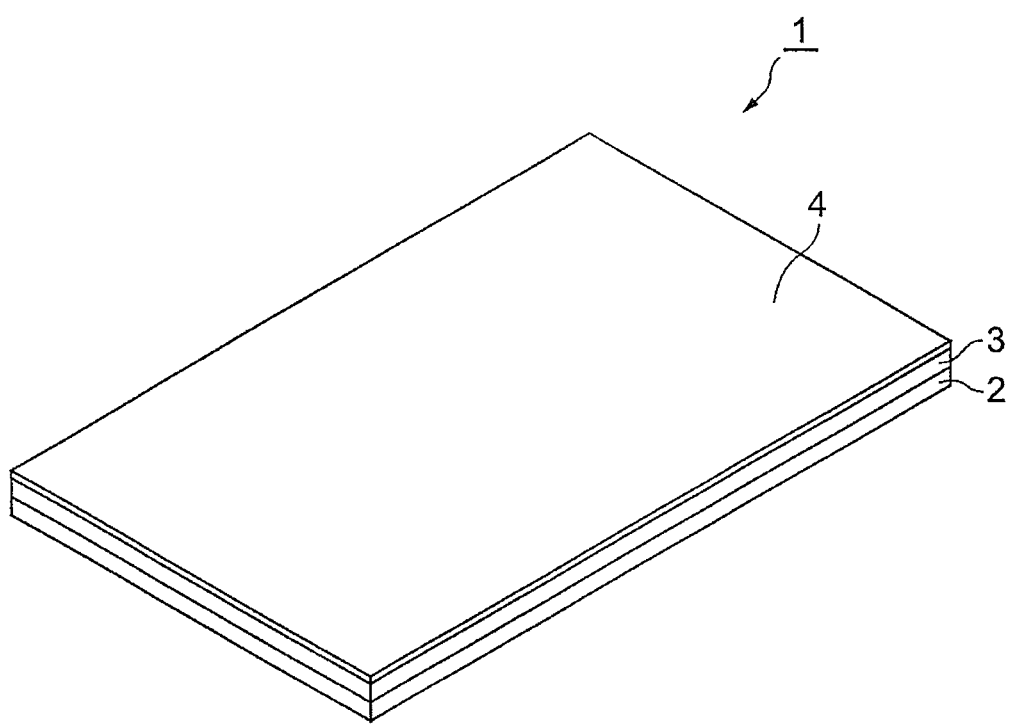

ADHESIVE SKIN PATCH AND PACKAGED PRODUCT

This is a National Phase Application filed under 35 U.S.C. 371 as a national stage of PCT/JP2009/052180, filed Feb. 9, 2009, an application claiming foreign priority benefits under 35 USC 119 of Japanese Application No. 2008-046805, filed on Feb. 27, 2008, the content of each of which is hereby incorporated by reference in its entirety.

TECHNICAL FIELD

The present invention relates to a patch and a packaging product for packaging the patch.

BACKGROUND ART

Ropinirole was developed as a drug which conquers the limit associated with L-Dopa therapy, and has been used for treating Parkinson's disease. Further, transdermal preparations containing ropinirole have been studied owing to the avoidance of adverse reactions on the stomach and intestines and the easy removal in case adverse reactions occur (Patent Documents 1 and 2).

On the other hand, the drug is distributed in the market in the form of an acid adduct salt from the viewpoints of the handleability and stability thereof. When a drug in the form of an acid adduct salt is directly applied for transdermal administration or the like, it is generally known that the absorbability tends to be decreased, but also known that a free form of a drug is preferred in terms of the absorbability.

In Patent Document 3, a technique wherein a drug acid adduct salt is used as a starting material for producing a transdermal preparation and the drug acid adduct salt is neutralized (desalted) in the preparation during the production or after the production so that a free form can be absorbed at the time of transdermal administration.

Patent Document 1: Japanese Unexamined Patent Application Publication (Translation of PCT Application) No. 2001-518058
Patent Document 2: Japanese Unexamined Patent Application Publication (Translation of PCT Application) No. H11-506462
Patent Document 3: Japanese Unexamined Patent Application Publication No. 2007-16020

DISCLOSURE OF THE INVENTION

Problems to be Solved by the Invention

However, when the present inventors attempted the production of a transdermal preparation having enhanced transdermal absorbability of ropinirole by using ropinirole hydrochloride as a drug and desalting the drug during the production or in the preparation, it was found that analogues of ropinirole are produced in the adhesive and pose a problem with the stability of the preparation.

Thus, an object of the present invention is to provide a patch which contains ropinirole and wherein the formation of the ropinirole analogue in the adhesive is prevented to a sufficient extent.

Means for Solving the Problems

The present invention provides a patch which comprises a backing layer and a pressure-sensitive adhesive layer formed on the backing layer wherein the pressure-sensitive adhesive layer contains (1) ropinirole and a metal salt produced by the reaction of a ropinirole acid adduct and a metal ion containing desalting agent in an equivalent mole or less to the acid adduct and (2) an adhesive base free of a hydroxyl group and a carboxy group.

Since the patch of the present invention contains a ropinirole free form produced by reacting a ropinirole acid adduct and a metal ion containing desalting agent so that the desalting agent is an equivalent mole or less to the ropinirole acid adduct, the patch has excellent transdermal absorbability of ropinirole as a drug. Further, since the patch contains the metal salt produced by the reaction in the above molar ratio and contains an adhesive base free of a hydroxyl group and a carboxy group as an adhesive base, the formation of ropinirole analogues which have a different retention time from that of ropinirole when measured by liquid chromatography is prevented to a sufficient extent. It is preferable that the pressure-sensitive adhesive layer be uncrosslinked. In this context, the styrene block aggregation of styrene block copolymers is not considered as crosslinking.

The metal salt produced during the production or after the production of the patch is applicable as the metal salt, and the preferable metal salt is at least one metal salt selected from the group consisting of metal chlorides, metal bromides, metal iodides and organic acid metal salts. Examples of the particularly preferable metal salt include at least one metal salt selected from the group consisting of sodium chloride, calcium chloride, aluminum chloride, stannous chloride, ferric chloride, magnesium chloride, potassium chloride, sodium citrate, sodium oxalate, sodium tartrate, sodium bromide and sodium succinate. When such a metal salt is used, the formation of ropinirole analogues in the pressure-sensitive adhesive layer is remarkably prevented.

It is preferred that the acid adduct be a hydrochloric acid adduct, an acetic acid adduct, a sulfuric acid adduct, a maleic acid adduct, an oxalic acid adduct, a citric acid adduct, a hydroiodic acid adduct, a hydrobromic acid adduct, a mesyl acid adduct, a tartaric acid adduct or a succinic acid adduct. With such a ropinirole acid adduct, metal chlorides, metal bromides, metal iodides and organic acid metal salts as listed as preferable metal salts can be easily obtained by using a metal ion containing desalting agent.

In the present invention, it is particularly preferable that the pressure-sensitive adhesive layer further contain an adsorbent which adsorbs a polar solvent contained in the layer. By allowing such an adsorbent to be contained, the impairment of the patch appearance caused by the excessive aggregation of the metal salt formed in the pressure-sensitive adhesive layer during the production or after the production can be prevented.

Due to such a good effect, the adsorbent is preferably at least one adsorbent selected from the group consisting of talc, kaoline, bentonite, hydrous silica, fumed silica, polyvinylpyrrolidone, propylene glycol, aminoalkyl methacrylate copolymers, crospovidone, carboxy vinyl polymers, lactic acid, acetic acid, zinc oxide, dextrin and dried aluminum hydroxide gel.

It is preferable that the patch described above be kept by being accommodated in a packaging product. In this instance, a packaging product capable of packaging the patch and a deoxidizer can prevent the formation of ropinirole analogues in the pressure-sensitive adhesive layer for an extended period of time.

Effect of the Invention

According to the present invention, a ropinirole containing patch wherein the formation of ropinirole analogues in the adhesive is prevented to a sufficient extent can be provided.

BRIEF DESCRIPTION OF THE DRAWINGS

FIG. 1 is a perspective view showing a preferable embodiment of the patch of the present invention.

DESCRIPTION OF SYMBOLS

1. Patch, 2. Backing layer, 3. Pressure-sensitive adhesive layer, 4. Release sheet

BEST MODES FOR CARRYING OUT THE INVENTION

Hereinafter, preferable embodiments are described in detail with reference to the drawing. A part of the drawing is depicted in a larger manner for easier understanding, and the size ratio does not necessarily correspond with that of the description.

FIG. 1 is a perspective view showing a preferable embodiment of the patch of the present invention. In FIG. 1, the patch 1 is provided with a backing layer 2, a pressure-sensitive adhesive layer 3 laminated on the backing layer 2, and a release sheet 4 attached on the pressure-sensitive adhesive layer 3. The pressure-sensitive adhesive layer 3 contains ropinirole, a metal salt as well as an adhesive base free of a hydroxyl group and a carboxy group. The metal salt can be obtained by the reaction of a ropinirole acid adduct and a metal ion containing desalting agent in an equivalent mole or less to the acid adduct.

The pressure-sensitive adhesive layer may be laminated to two or more layers, and may be laminated not only on one side but also on both sides of the backing layer. When a plurality of the pressure-sensitive adhesive layer are present, at least one of them may be the pressure-sensitive adhesive layer 3 described above. In the present embodiment, since the patch is provided with a release sheet 4, the release sheet 4 is removed at the time of application for use.

The material for the backing layer 2 is not limited insofar as it is a material typically used for patches, and elastic or non-elastic materials can be used. Specific examples of the preferably used material include films or sheets formed with a synthetic resin such as polyethylene terephthalate, polyethylene, polypropylene, polybutadiene, ethylene vinyl acetate polymer, polyvinyl chlorides, polyesters, nylon, and polyurethane, or laminates thereof, porous membranes, foams, fabrics and nonwoven fabrics and paper materials.

The adhesive base contained in the pressure-sensitive adhesive layer 3 is preferably those free of a hydroxyl group and a carboxy group. When the pressure-sensitive adhesive layer contains a hydroxyl group or a carboxy group, the formation of ropinirole analogues in the adhesive cannot be prevented sufficiently. Examples of such an adhesive base include acrylic adhesive bases, rubber adhesive bases, and silicone adhesive bases.

Examples of the preferably usable acrylic adhesive base include homopolymer or copolymer of (meth)acrylate ester, and copolymer of alkyl (meth)acrylate ester and other functional monomers. The (meth)acrylate ester is preferably alkyl (meth)acrylate ester, and the alkyl group in the compound has preferably 1 to 22 carbons, more preferably 2 to 18 carbons, further preferably 4 to 12 carbons. Other functional group monomers used for forming a copolymer include vinyl ester such as vinyl acetate, vinyl ether, styrene, and methyl styrene.

The acrylic adhesive is preferably a copolymer of an acrylic ester and vinyl acetate. An example of such an acrylic adhesive is, among the National Starch and Chemical Company Duro-TAK acrylic adhesive series, the grade free of a hydroxyl group and a carboxy group (Non-Functional group).

As the rubber adhesive base, natural rubbers and synthetic rubbers can be used, and examples that are preferably used include synthetic rubbers that are free of a hydroxyl group and a carboxy group such as styrene-isoprene-styrene block copolymer (hereinafter abbreviated as "SIS"), isoprene rubber, polyisobutylene (hereinafter abbreviated as "PIB"), styrene-butadiene-styrene block copolymer (hereinafter abbreviated as "SBS"), styrene-butadiene rubber (hereinafter abbreviated as "SBR"), and polybutene. These adhesive bases are usually used by adding a tackifier thereto.

Usable silicone adhesive bases are those containing polydimethyl siloxane or the like as a main component, and usually used by adding a tackifier such as MQ resin thereto.

Among the adhesive bases listed above, SIS free of a hydroxyl group and a carboxy group and acrylic ester copolymers are preferable in respect of preventing the formation of ropinirole analogues.

These adhesive bases may be used singly, or two or more thereof may be used in combination. For the combination of the adhesive bases, the mixture wherein SIS and MB are mixed in a mass ratio of 9:1 to 1:1 is preferable. The amount of an adhesive base to be added is preferably 10 to 95% by mass, more preferably 15 to 80% by mass, particularly preferably 20 to 70% by mass, on the basis of the total mass of the pressure-sensitive adhesive layer 3 when considering the formation of the pressure-sensitive adhesive layer 3 and the tissue permeability of the active ingredients.

In the pressure-sensitive adhesive layer 3 of the patch 1, ropinirole and the metal salt produced by the reaction of a ropinirole acid adduct and a metal ion containing desalting agent in an equivalent mole or less to the acid adduct are contained, in addition to the above-mentioned adhesive base.

Ropinirole includes those remained in the form of salt due to an incomplete neutralization in addition to those which became a free form by a neutralization reaction during the production steps to be described later or in the preparation.

The metal salt contained in the pressure-sensitive adhesive layer is preferably those produced during the production steps or in the preparation. The pressure-sensitive adhesive layer may contain a metal salt other than those produced during the production steps or in the preparation.

Considering that the sufficient potency is attained as a patch, the preparation properties and tissue absorbability, ropinirole is added in a proportion of preferably 0.5 to 50% by mass, particularly preferably 1 to 30% by mass, on the basis of the total mass of the pressure-sensitive adhesive layer 3.

In the present invention, the ropinirole free form with a higher tissue absorbability can be made present in the pressure-sensitive adhesive layer at the time of preparation application as a result of the neutralization reaction wherein a ropinirole acid adduct is used as a starting material of the production and mixed in a production step with a metal ion containing desalting agent (neutralizer) such as alkali metal hydroxides. Consequently, in the pressure-sensitive adhesive layer of the patch, the metal salt produced by the neutralization reaction is also present.

The metal salt is not limited insofar as it is produced by the above desalting (neutralization) reaction and is accordingly determined based on the metal ion containing desalting agent (neutralizer) for neutralizing a ropinirole acid adduct salt and a metal salt. It is preferred that the metal salt be at least one selected from metal chlorides, metal bromides, metal iodides and organic acid metal salts. Among these, it is particularly preferred that the metal salt be one or two or more selected from sodium chloride, calcium chloride, aluminum chloride, stannous chloride, ferric chloride, magnesium chloride, potassium chloride, sodium citrate, sodium oxalate, sodium tartrate, sodium bromide and sodium succinate.

The metal ion containing desalting agent used in the desalting (neutralization) reaction of the patch is preferably an alkali metal hydroxide. The alkali metal hydroxide is added to convert a ropinirole acid adduct salt as a whole or a part to the state of free base. To obviate the decomposition of the drug caused by an excessive amount of a metal ion containing desalting agent at this step, the metal ion containing desalting agent is preferably added within a range from 0.5 to 4 equivalent amounts to the equivalent amount of the drug acid base. The addition may be carried out once during the production steps, or carried out in several times in a divided manner.

Specific examples of the metal ion containing desalting agent include sodium hydroxides, potassium hydroxides, magnesium hydroxides, with sodium hydroxides being preferable among these. These are added to convert a drug to a free form but when the metal ion containing desalting agent (sodium hydroxide or the like) is added in an amount exceeding the equivalent mole of a ropinirole acid adduct (ropinirole hydrochloride or the like), a large amount of analogues is formed and tends to cause the coloring of the base, whereas the desalting agent of less than an equivalent mole decreases the formation of the analogues and tends not to develop the coloring.

Consequently, to obviate the decomposition of a drug caused by an excessive amount, the metal ion containing desalting agent is preferably added during the production step within a range from 0.5 to 1 equivalent amount to the equivalent amount of the acid base of a ropinirole acid adduct, and, as a result, the metal salt is present in the equivalent mole or less of the drug in the pressure-sensitive adhesive layer of the patch as a final product. The addition of the metal ion containing desalting agent may be carried out several times in a divided manner during the production steps.

Further, the metal salt produced by the neutralization reaction as described above tends to aggregate and grow as crystals due to the polar solvent such as water which is used in the production steps and remained in a very small amount in the pressure-sensitive adhesive layer. Thus, to prevent such a crystal aggregation and growth or to disperse the crystal uniformly, it is also possible to contain an adsorbent (hygroscopic inorganic and/or organic substances) in the pressure-sensitive adhesive layer.

In the present invention, it is preferred that an adsorbent be contained in the pressure-sensitive adhesive layer 3. By containing an adsorbent, the aggregation and growth of the metal salt crystal caused by the neutralization reaction can be prevented, and the crystal can be uniformly dispersed.

The adsorbent is not limited insofar as it has the effect of the present invention, and among the additives listed in "Japanese Pharmaceutical Excipients Directory 2000, published on Apr. 28, 2000, 1st edition", the inorganic substances and organic substances described as having hygroscopic properties, dampproofing properties and adsorptive properties are applicable as well as aminoalkyl methacrylate copolymer and zinc oxide, which are not described in the above "Japanese Pharmaceutical Excipients Directory 2000" but have been known to have adsorptive properties.

Among these, examples preferably usable include minerals such as talc, kaoline, and bentonite; silicone compounds such as fumed silica (Aerosil (registered trademark), etc.) and hydrous silica; metal compounds such as zinc oxide and dried aluminum hydroxide gel; weak acids such as lactic acid and acetic acid, sugars such as dextrin, and polymers such as polyvinylpyrrolidone, propylene glycol, aminoalkyl methacrylate copolymer, crospovidone, and carboxy vinyl polymer. These adsorbents may be used in combination of two or more as necessary.

The content of the adsorbent contained in the pressure-sensitive adhesive layer 3 is preferably 0.5 to 50% by mass on the total mass basis of the pressure-sensitive adhesive layer 3. A content of 0.5% by mass or lower tends not to achieve sufficient effects to prevent the aggregation and growth of the metal salt crystal or to disperse the crystal uniformly. Conversely, a content of 50% by mass or higher has a tendency of reducing the adhesion of the pressure-sensitive adhesive layer 3, likely making it difficult to apply the patch.

The patch 1 of the present invention may contain as necessary, in addition to the above compositions, tackifier, plasticizer, absorption enhancer, antioxidant, filler, preservative, ultraviolet absorber and drug crystal precipitation inhibitor.

Examples of the usable tackifier include rosin resins such as "Ester Gum (tradename, Arakawa Chemical Industries, Ltd.)", "Hariester (tradename, Harima Chemicals, Inc.)", "Pentalyn (tradename, Eastman Chemical Company)" and "Foral (tradename, Eastman Chemical Company)", terpene resins such as "YS resin (tradename, Yasuhara Chemical Co., Ltd.)" and "Piccolyte (tradename, Loos and Dilworth)", petroleum resins such as "Arkon (tradename, Arakawa Chemical Industries, Ltd.)", "Regalrez (tradename, Eastman Chemical Company)", "Piccolastic (tradename, Eastman Chemical Company)", "Escorez (tradename, ExxonMobil Chemical Company)", "Wingtack (tradename, Goodyear)" and "Quintone (tradename, Zeon Corporation)", phenol resins and xylene resins.

These tackifiers may be used singly or in combination of two or more. The amount of the tackifier to be added is preferably 10 to 90% by mass, more preferably 15 to 70% by mass, particularly preferably 20 to 60% by mass, on the basis of the total mass of the pressure-sensitive adhesive layer 3, when considering the sufficient adhesion of and the local irritation when removing the patch 1.

Examples of the plasticizer include petroleum oils such as paraffin process oils, naphthene process oils, and aromatic process oils; squalene, squalene; plant oils such as olive oil, camellia oil, castor oil, tall oil, and peanut oil; dibasic esters such as dibutyl phthalate and dioctyl phthalate; liquid rubbers such as polybutene and liquid isoprene rubber; diethylene glycol, polyethylene glycol, propylene glycol, and dipropylene glycol. These plasticizers can be used singly or two or more can be used in combination. In the embodiment of the present invention, it is preferable to use the liquid paraffin and liquid polybutene.

The content of the above plasticizer in the pressure-sensitive adhesive layer 3 is preferably 5 to 60% by mass, more preferably 10 to 50% by mass, particularly preferably 15 to 40% by mass, on the basis of the total mass of the pressure-sensitive adhesive layer 3, considering the maintenance of the sufficient adhesion as the patch 1.

Examples of the preferably used absorption enhancer include fatty alcohols such as isostearyl alcohol, fatty acids such as capric acid, fatty acid derivatives such as propyleneglycol monolaurate, isopropyl palmitate, and isopropyl myristate, propylene glycol, polyethylene glycol, and lauric acid diethanolamine. Among these, lower alcohol esters of fatty acids such as isopropyl palmitate can be particularly preferably used. These absorption enhancers may be used singly, or in combination of two or more. The content of the absorption enhancer to be added is preferably 1 to 30% by mass, more preferably 3 to 20% by mass, particularly preferably 5 to 15% by mass, on the basis of the total mass of the pressure-sensitive adhesive layer 3, considering sufficient permeability of the active ingredients to the tissue and the local irritation and the like, as a preparation.

Examples of the usable antioxidant include tocopherols and ester derivatives thereof, ascorbic acid, ascorbyl stearate, nordihydroguaiaretic acid, dibutylhydroxytoluene (hereinafter abbreviated as BHT), and butylated hydroxyanisole, with BHT being particularly preferably used.

Examples of the filler include aluminum hydroxide, calcium carbonate, magnesium carbonate; silicates such as aluminum silicate and magnesium silicate; silicic acid, barium sulfate, calcium sulfate, calcium zincate, zinc oxide, and titanium oxide.

Examples of the preservative include disodium edetate, tetrasodium edetate, ethyl parahydroxybenzoate, propyl parahydroxybenzoate, and butyl parahydroxybenzoate.

Examples of the ultraviolet absorber include p-aminobenzoic acid derivatives, anthranilic acid derivatives, salicylic acid derivatives, coumarin derivatives, amino acid compounds, imidazoline derivatives, pyrimidine derivatives, and dioxane derivatives.

Examples of the drug crystallization inhibitor include fatty alcohols such as oleyl alcohol, lauryl alcohol, octyldodecanol, and isostearyl alcohol, macromolecules such as cyclodextrins, silicon dioxide, polyvinylpyrrolidone, and cellulose derivatives, with fatty alcohols being particularly preferable.

The above-mentioned antioxidants, fillers, preservatives and ultraviolet absorbers can be added in a total amount of preferably 5% by mass or less, more preferably 3% by mass or less, particularly preferably 1% by mass or less, on the basis of the total mass of the pressure-sensitive adhesive layer 3.

Next, an example of the production process of the patch 1 of the present embodiment will be described.

First, a mixture for forming a pressure-sensitive adhesive layer 3 is prepared. Using a mixer, the above-mentioned adhesive base, a ropinirole acid adduct, a metal ion containing desalting agent and other optional ingredients are dissolved or dispersed in a solvent of the adhesive base to obtain a mixture for forming the pressure-sensitive adhesive layer 3.

Examples of the usable solvent for the adhesive base include toluene, hexane, ethyl acetate, cyclohexane, heptane, butyl acetate, ethanol, methanol, and xylene, isopropanol. These are selected as necessary in accordance with the ingredients to be dissolved or dispersed, and may be used singly or in combination of two or more.

Subsequently, the obtained mixture for forming the pressure-sensitive adhesive layer 3 is spread directly on a backing layer 2 to form the pressure-sensitive adhesive layer 3, or the mixture is spread on a release-treated paper or film to form the pressure-sensitive adhesive layer 3 and the backing layer 2 is placed thereon, followed by the press-bonding transfer of the pressure-sensitive adhesive layer 3 to the backing layer 2. Next, a release sheet 4 for protecting the pressure-sensitive adhesive layer 3 is adhered on the pressure-sensitive adhesive layer 3 to obtain the patch 1. Further, the thickness of the pressure-sensitive adhesive layer is preferably 30 to 250 μm, more preferably 50 to 150 μm. A thickness of 30 μm or less tends to diminish the sustainability of the drug release, whereas a thickness of 250 μm or more increases the amount of the drug contained in the pressure-sensitive adhesive layer despite the constant release and tends to make the production cost comparatively expensive.

In the package for packaging the above described ropinirole containing patch, the formation of the ropinirole analogues can further be effectively prevented by containing a deoxidizer together with the patch. Accordingly, in the package for packaging the ropinirole containing patch, it is preferable to provide a ropinirole patch containing package in which a deoxidizer is further contained therewith.

The package is not limited insofar as it is a common package for packaging a drug containing patch, and plastic packages, plastic packages with a metal layer (e.g., an aluminum layer) formed and metal packages (e.g., aluminum package) are preferable.

Applicable deoxidizers are those using iron powder and those containing vitamin C as the main ingredient. Specific examples include Ageless series (Mitsubishi Gas Chemical Company, Inc.) and PharmaKeep series (Mitsubishi Gas Chemical Company, Inc.).

EXAMPLES

Hereinafter, the present invention will be specifically described with reference to Examples and Comparative Examples, but is not limited thereto.

Example 1

Using a mixer, ropinirole hydrochloride, sodium hydroxide (base), liquid paraffin and toluene (solvent) were mixed in advance, and a separately prepared mixed solution of SIS (JSR Corporation, SIS5000, a hydroxyl group and a carboxy group are not contained), an alicyclic hydrocarbon resin and toluene was added thereto and mixed to obtain an adhesive solution. The solution was spread on release-treated film to dry and remove the solvent, thereby forming a pressure-sensitive adhesive layer having a thickness of 100 μm. A backing layer was placed on the layer and the pressure-sensitive adhesive layer was subjected to press-bonding transfer to obtain a patch. The composition and the amount of the base to ropinirole hydrochloride are as shown in Table 1.

Example 2

A patch was produced in the same manner as in Example 1 except that the composition was made as shown in Table 1. The base amount to ropinirole hydrochloride is as shown in Table 1.

Comparative Example 1

A patch was produced in the same manner as in Example 1 except that the composition was made as shown in Table 1. The base amount to ropinirole hydrochloride is as shown in Table 1.

TABLE 1

|  | Example 1 | Example 2 | Comparative Example 1 |
|---|---|---|---|
| Ropinirole hydrochloride | 5.0 parts by mass | 5.0 parts by mass | 5.0 parts by mass |
| Sodium hydroxide | 0.5 parts by mass | 0.6 parts by mass | 0.8 parts by mass |
| SIS | 24.2 parts by mass | 24.2 parts by mass | 24.2 parts by mass |
| Alicyclic hydrocarbon resin | 41.2 parts by mass | 41.2 parts by mass | 41.2 parts by mass |
| Liquid paraffin | 29.1 parts by mass | 29.1 parts by mass | 29.1 parts by mass |
| Base amount to ropinirole hydrochloride | 0.75 times mole | 0.9 times mole | 1.1 times mole |

Content measuring method of base component and unknown compounds

In accordance with the procedure described below, the status of occurrence of ropinirole analogues was checked. The results of Examples 1 and 2 and Comparative Example 1 are as shown in Table 2 below.

A patch punched out to 10 cm$^2$ was placed in a 50 mL centrifugation tube and 10 mL of tetrahydrofrane was added thereto to dissolve the pressure-sensitive adhesive layer. After adding a mixed solution of water/methanol thereto to give 50 mL, the mixture was subjected to high performance liquid chromatography (HPLC) and the content of ropinirole and the unknown compounds which appeared on the chromatochart was measured. In the table, the ropinirole content (main drug content) is shown in the proportion to the amounts which are theoretically supposed to be contained in the preparations. The indications of the unknown compounds in the table are shown by the retention time on the chromatochart (e.g. an unknown compound having a retention time of 10.2 min is 10.2), and the content of each unknown compound is shown in the content ratio to ropinirole. Further, when not detected, "–" is shown, and when detected only 0.05% or less, "tr" is shown.

TABLE 2

| | Drug content (%) (to theoretical value) | | | | |
|---|---|---|---|---|---|
| | Base component | Unknown compound (retention time) | | | |
| | | 5.5 | 7 | 13.1 | Total |
| Example 1 | 103.2 | — | — | — | 103.2 |
| Example 2 | 102 | — | — | — | 102 |
| Comparative Example 1 | 101.2 | tr | 0.17 | 0.17 | 101.5 |

Example 3

Using a mixer, ropinirole hydrochloride, sodium hydroxide (base), liquid paraffin and methanol (solvent) were mixed in advance, and an acrylic adhesive solution Duro-TAK 87-900A (National Starch and Chemical Company, product name, no hydroxyl group or carboxy group contained) was added to and mixed with the mixture to obtain an adhesive solution. The solution was spread on a release-treated film to dry and remove the solvent, thereby forming a pressure-sensitive adhesive layer. A backing layer was placed on the layer and the pressure-sensitive adhesive layer was subjected to press-bonding transfer to obtain a patch. Further, in accordance with the "Content measuring method of base component and unknown compounds" described above, the status of the occurrence of the ropinirole analogues was checked. The composition and the base amount to ropinirole hydrochloride are as shown in Table 3 below and the test results are as shown in Table 4.

Comparative Example 2

A patch was obtained in the same manner as in Example 3 except that Duro-TAK 87-900A was replaced with Duro-TAK 87-2516 (National Starch and Chemical Company, product name, a hydroxyl group contained), and the same test as conducted in Example 3 was carried out. The base amount to ropinirole hydrochloride are as shown in Table 3 below and the test results are as shown in Table 4.

Comparative Example 3

A patch was obtained in the same manner as in Example 3 except that Duro-TAK 87-900A was replaced with Duro-TAK 87-2194 (National Starch and Chemic al Company, product name, a carboxy group contained), and the same test as conducted in Example 3 was carried out. The base amount to ropinirole hydrochloride are as shown in Table 3 below and the test results are as shown in Table 4.

TABLE 3

|  | Example 3 | Comparative Example 2 | Comparative Example 3 |
|---|---|---|---|
| Ropinirole hydrochloride | 5.0 parts by mass | 5.0 parts by mass | 5.0 parts by mass |
| Sodium hydroxide | 0.5 parts by mass | 0.5 parts by mass | 0.5 parts by mass |
| Duro-TAK 87-900A | 94.5 parts by mass | — | — |
| Duro-TAK 87-2516 | — | 94.5 parts by mass | — |

TABLE 3-continued

|  | Example 3 | Comparative Example 2 | Comparative Example 3 |
|---|---|---|---|
| Duro-TAK 87-2194 | — | — | 94.5 parts by mass |
| Base amount to ropinirole hydrochloride | 0.75 times mole | 0.75 times mole | 0.75 times mole |

TABLE 4

| | Drug content (%) (to theoretical value) | | | | | |
|---|---|---|---|---|---|---|
| | Base component | Unknown compound (retention time) | | | | Total |
| | | 3.3 | 7.5 | 9.9 | 10.2 | 18.6 | |
| Example 3 | 104.1 | — | — | — | — | 0.43 | 104.5 |
| Comparative Example 2 | 97.6 | 0.08 | 0.42 | — | 0.08 | — | 98.2 |
| Comparative Example 3 | 92.9 | 2.31 | 0.39 | 0.18 | tr | — | 95.8 |

Example 4

A patch was obtained in the same manner as in Example 1 except that Aerosil (registered tradename), an adsorbent, was added to the mixed solution of SIS, an alicyclic hydrocarbon resin and toluene as in Example 1. Further, the content of Aerosil was 5 parts by mass and other component ratios were the same as in Example 1.

Examples 5 to 30

Patches were obtained in the same manner as in Example 4 except that the compounds of Table 5 were added in place of Aerosil used in Example 4.

(Evaluation of Metal Salt Aggregate)

The appearances of the patches of Examples 1 and 4 to 30 were examined and evaluated for the presence of aggregates of the metal salt crystal with naked eyes. The type and content of the adsorbents and evaluation results are shown in Table 5. The patches wherein no aggregates were found are indicated as "a", those wherein small aggregates having an average particle size of 100 to 250 μm were found are indicated as "b", and those wherein aggregates having an average particle size of exceeding 250 μm were found are indicated as "c".

TABLE 5

| | Adsorbent | Content [Mass part] | Result |
|---|---|---|---|
| Example 1 | None | 0 | c |
| Example 4 | Aerosil (registered tradename) | 5 | a |
| Example 5 | Aminoacryl methacrylate copolymer | 5 | a |
| Example 6 | Crospovidone | 5 | a |
| Example 7 | Lactic acid | 5 | a |
| Example 8 | Talc | 5 | a |
| Example 9 | Dextrin | 5 | b |
| Example 10 | Propylene glycol | 5 | b |
| Example 11 | Polyvinylpyrrolidone | 5 | b |
| Example 12 | Iostearic acid | 5 | c |
| Example 13 | Oleic acid | 5 | c |
| Example 14 | Sorbitan monolaurate | 5 | c |
| Example 15 | Sorbitan oleate | 5 | c |
| Example 16 | Isopropyl myristate | 5 | c |
| Example 17 | Isopropyl palmitate | 5 | c |
| Example 18 | Hexyl laurate | 5 | c |
| Example 19 | Glycerol monooleate | 5 | c |
| Example 20 | Triacetin | 5 | c |
| Example 21 | Lauryl alcohol | 5 | c |
| Example 22 | Myristyl alcohol | 5 | c |
| Example 23 | Oleyl alcohol | 5 | c |
| Example 24 | Polybutene | 5 | c |
| Example 25 | Propylene glycol monolaurate | 5 | c |
| Example 26 | Tween 80 (registered trademark) | 5 | c |
| Example 27 | Lauric acid diethanolamide | 5 | c |
| Example 28 | Isostearyl alcohol | 5 | c |
| Example 29 | Octyldodecanol | 5 | c |
| Example 30 | Benzyl alcohol | 5 | c |

The invention claimed is:

1. A patch comprising a backing layer and a pressure-sensitive adhesive layer formed on the backing layer, the pressure-sensitive adhesive layer containing:
   ropinirole and a metal salt produced by a reaction of a ropinirole acid adduct and a metal ion containing desalting agent in an equivalent mole or less to the acid adduct;
   an adhesive base free of a hydroxyl group and a carboxy group; and
   an adsorbent selected from the group consisting of fumed silica, aminoacryl methacrylate copolymer, crospovidone, lactic acid, talc, dextrin, propylene glycol, and polyvinylpyrrolidone, which adsorbs a polar solvent contained in the pressure-sensitive adhesive layer, wherein the adsorbent suppresses aggregation and growth of the metal salt; and wherein the adsorbent is present in a concentration of 0.5 to 5% by mass on the total mass basis of the pressure-sensitive adhesive layer.

2. The patch according to claim 1, wherein the metal salt is one produced during the production or after the production of the patch.

3. The patch according to claim 1, wherein the metal salt is at least one metal salt selected from a group consisting of metal chlorides, metal bromides, metal iodides, and organic acid metal salts.

4. The patch according to claim 1, wherein the metal salt is at least one metal salt selected from a group consisting of sodium chloride, calcium chloride, aluminum chloride, stannous chloride, ferric chloride, magnesium chloride, potassium chloride, sodium citrate, sodium oxalate, sodium tartrate, sodium bromide and sodium succinate.

5. The patch according to claim 1, wherein the acid adduct is a hydrochloric acid adduct, an acetic acid adduct, a sulfuric acid adduct, a maleic acid adduct, an oxalic acid adduct, a citric acid adduct, a hydroiodic acid adduct, a hydrobromic acid adduct, a mesyl acid adduct, a tartaric acid adduct, or a succinic acid adduct.

6. A packaging product packaging the patch according to claim 1 and a deoxidizer.

7. The patch according to claim 1, wherein the pressure-sensitive adhesive layer contains 0.5 to 50% by mass of ropinirole on the basis of the total mass of the pressure-sensitive adhesive layer.

8. The patch according to claim 1, wherein the pressure-sensitive adhesive layer contains 1 to 30% by mass of ropinirole on the basis of the total mass of the pressure-sensitive adhesive layer.

9. The patch according to claim 1, wherein the metal ion containing desalting agent is added to the reaction within a range from 0.5 to 1 equivalent amount to the equivalent amount of acid base of the ropinirole acid adduct.

\* \* \* \* \*